United States Patent [19]

Schindler et al.

[11] 4,235,231
[45] Nov. 25, 1980

[54] PORTABLE ARTIFICIAL KIDNEY

[75] Inventors: Johannes G. Schindler, Marburg; Wilfried Schael, Bad Homburg von der Hohe, both of Fed. Rep. of Germany

[73] Assignee: Dr. E. Fresenius Chemisch Pharmazeutische Industrie KG, Bad Homburg van der Hohe, Fed. Rep. of Germany

[21] Appl. No.: 928,859

[22] Filed: Jul. 28, 1978

[30] Foreign Application Priority Data

Jul. 29, 1977 [DE] Fed. Rep. of Germany ....... 2734248

[51] Int. Cl.³ ............................................. B01D 13/00
[52] U.S. Cl. ................................. 128/214 R; 128/348
[58] Field of Search ............ 128/213 A, 214.2, 214 B, 128/214 R, 348, 349 B, 349 R, 632, 673, 748; 3/1; 210/321 B, 22, DIG. 23

[56] References Cited

U.S. PATENT DOCUMENTS

| 2,936,761 | 5/1960 | Snyder | 128/349 B |
|---|---|---|---|
| 3,489,647 | 1/1970 | Kolobow | 3/1 X |
| 3,512,517 | 5/1970 | Kadish et al. | 128/214 R |
| 3,520,298 | 7/1970 | Lange | 128/240 X |
| 3,623,960 | 11/1971 | Williams | 128/635 X |
| 3,640,269 | 2/1972 | Delgado | 128/769 X |
| 3,658,053 | 4/1972 | Fergusson et al. | 128/632 |
| 3,981,299 | 9/1976 | Murray | 128/349 B |
| 4,094,775 | 6/1978 | Mueller | 210/321 B X |

FOREIGN PATENT DOCUMENTS

1280481  3/1960  France ............................... 128/349 B

OTHER PUBLICATIONS

Boen et al., "Periodic Peritoneal Dialysis in the Management of Chronic Uremia", *Trans. Amer. Soc. Artif. Inter. Orgs.,* vol. III, 1962 (pp. 256-262).

*Primary Examiner*—Robert W. Michell
*Assistant Examiner*—Jeffrey W. Tayon
*Attorney, Agent, or Firm*—Omri M. Behr; Martin Sachs

[57] ABSTRACT

A portable artificial kidney designed for continuous use includes a catheter with filter properties. The body portion of the catheter has an infusion duct which opens into the surface of the catheter and is provided with surface channels which are covered by a semi-permeable membrane. Ducts are provided which communicate with the channels. One duct is operatively coupled to a suction pump to remove the filtrate. Another duct serves to supply a rinsing solution and the infusion duct serves to replace the liquid which has been filtered off.

9 Claims, 1 Drawing Figure

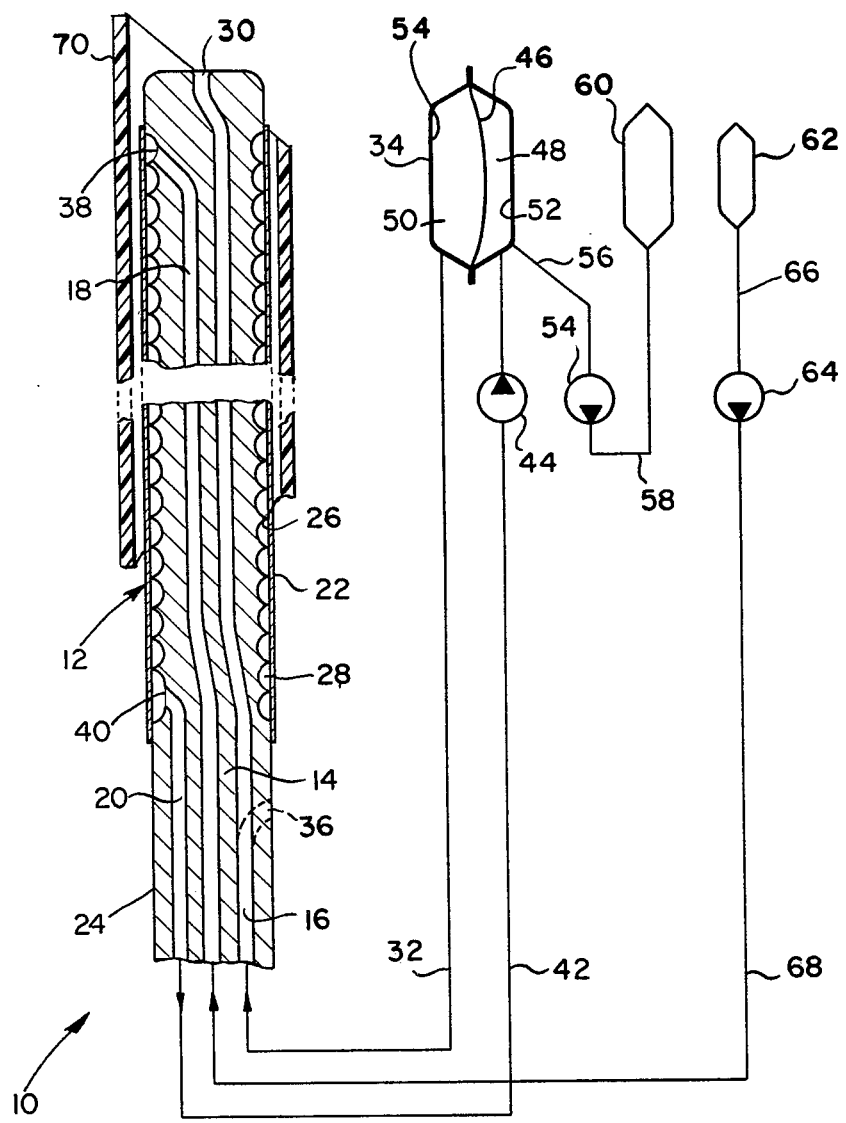

PORTABLE ARTIFICIAL KIDNEY

BACKGROUND OF THE INVENTION

1. Field of the Invention

The present invention relates to a mechanical devices for replacing the natural functions of kidneys, and in particular, is related to a portble artificial kidney designed for continuous use and worn on the body of the patient.

2. Description of the Prior Art

Different types of artifical kidneys are presently known in the art. Generally, they contain a material exchanger which is placed somewhere in the circulating blood stream and include a semi-permeable membrane. An external liquid system functions to collect the materials passed out from the blood and replaces the quantity of liquid which has been removed. Large amounts of fluid must be separated out of the blood, and until now, all the devices in use are stationary devices which are rather large and require the patient to be connected thereto, for example, three times per week for several hours in each case. Although there has been a great need for a portable material exchanger to function as an artifical kidney, none have been available until the present time, which may be worn by the patient and used continually.

The method predominately used in the prior art was based upon the principle of dialysis. With dialysis, the patient's blood is passed along on one side of a semi-permeable membrane and a dialyzing solution of suitable composition is passed along on the other side. The material exchange, more particularly the transition (transfer) of uriniferous substances out of the blood through the semi-permeable membrane into the dialyzing solution, is thus predominately a process of diffusion.

In recent years another method has proved to be suitable to accomplish the same purpose. This method utilizes convective transportation of material, is called diafiltration or hemofiltration and provides for the drawing off from the patient of fairly large quantities of plasma water with uriniferous substances dissolved therein. The plasma water is drawn off through a filter membrane having a pressure differential thereacross. Simultaneously with the drawing off of the plasma water a replacement fluid is infused with a suitable replacement solution until the patient's fluid balance is normalized (brought back to normal). This method is more effective than the dialysis process when suitable filters are utilized, because less quantities of fluid need be withdrawn in order to obtain the same effective amount of filtering. With dialysis treatment approximately 160 liters of dialyzing solution are required, whereas to obtain the equivalent hemofiltration approximately 15 liters of substution solution are sufficient. In the future, it is expected that by using ketoamino acids together with hemofiltration this quantity of fluid may be reduced still further, since the nitrogen contained in the lower molecular weight uriniferous substance may be partially returned to the patient. As a result, the concentrations of lower molecular weight poisons occurring in the urine, which were previously a factor in obtaining further reduction of the fluid exchange, can be lowered initially.

With the type of hemofiltration previously used the treatment takes place discontinuously in a manner similar to hemodialysis and, in fact, generally takes place for periods of five hours, three times per week. Typically, approximately 17 liters of filtrate are drawn off per treatment and approximately 15 liters of substitution solution are supplied. Extending the duration of a treatment beyond approximately five hours is not practicable. As a result of the dilution effect of the substitute solution the effectiveness drops considerably in the course of treatment. The concentration of uriniferous substances in the filtrate is reduced to approximately one-third if this time period is extended. The average or mean value of the concentrate in the filtrate is approximately equal to 60% of that occurring at the start. Because of the limited difusion speed, the washing of the uriniferous substance out of the intercellular area proceeds slowly.

With a continuous treatment method, according to the principles of the present invention, the dilution effect is insignificant so that the same effective treatment is achieved with a small fluid exchange. The discontinuous application of the prior art method requires approximately three times seventeen liters of filtrate or about 50 liters in total. With the continuous filtration method, the quantity of filtrate required is only approximately 30 liters to remove the same quantity of uriniferous substances from the blood stream. This corresponds to a filtrate flow of approximately 3 milliliters per minute which can be achieved with a relatively small filter surface area.

The prior art techniques which require providing a connection between the circulation of the patient's blood and the filter, which is normally placed outside the body, represents a substantial problem. Generally, two hollow hypodermic needles are used; one for supplying the blood and one for returning the blood into the body. In order to obtain a sufficiently low flow through resistance, the diameter of these hypodermic needles are approximately 1.8 to 2.4 milimeters. Repeated puncturing with these large hollow needles is very painful for the patient and involves permanent damage to the tissue and the blood vessels punctured. This fact, in addition to the preceding quantitative observations with respect to the utilization of continuous filtration techniques, led to the development of a filter catheter which can be placed inside the blood circulation system of the patient for relatively large periods of time.

SUMMARY OF THE INVENTION

The present invention overcomes the shortcomings found in the prior art by providing a cheap artifical kidney which the patient can carry constantly on or in his body without being limited inconveniently in his freedom of movement. The preferred embodiment of the present invention is constructed so that it requires a minimum of control and reservoir elements in order to be miniturized and uncomplicated.

A portable artifical kidney, for use in a living being, according to principles of the present invention, comprises a catheter filter adapted to be inserted into the circulating blood stream members of a living being to obtain a continuous flow of filtered liquid. The catheter filter includes a body portion with at least three ducts disposed therein, each providing a liquid flow path to the surface of the body portion. A semi-permeable membrane circumscribes part of the body portion and functions to the blood stream and provide a filtrate. A suction device is operably coupled to one of the ducts to draw off the filtrate. A reservoir is operatively coupled to the suction device and communicates with a second duct. The reservoir discharges its contents into the second duct in an amount essentially equal to the amount of the filtrate received into the reservoir, via the first duct. A third duct is supplied with a liquid communicating with the inner surface of the filter membrane in order to rinse the membrane.

BRIEF DESCRIPTION OF THE DRAWING

In order that the invention may be more fully understood, it will now be described, by way of example, with reference to the sole accompanying drawing which shows a longitudinal section of the catheter filter and a schematic presentation of the external system carrying fluid cooperating with the catheter.

DESCRIPTION OF THE PREFERRED EMBODIMENT

A portable artifical kidney 10, according to the principles of the present invention, as shown in the sole FIGURE includes a catheter 12 having a body portion 14 which is sufficiently small in size permitting it to be introduced into a patient's blood vessel (preferably into the vena cava with access via the vena saphena magna). The technique of introducing vessel catheters and the auxilliary means suitable for this are known in the art.

The catheter body portion 14 is fabricated from a flexible but rigid material such as, for example, polyamide or polyester and has at least three internal ducts 16, 18 and 20 running longitudinally therein and are described in detail below. The catheter 12 preferably has an outside diameter of approximately four millimeters and an active length of 350 millimeters. The connection of the internal ducts 16, 18 and 20 of the body portion 14 to the external tubing is conventional and not shown. The body portion 14 of the catheter 12 is covered for the most part on its outer surface with a semi-permeable membrane 22 which is supported on the surface 24 of the body portion 14 by the ribs or walls 26 which remain after a spiral channel 28 is cut into the surface 24 of body portion 14.

The duct 16 which runs inside the catheter body portion 14 terminates in an opening 30 providing direct communication in a fluid flow path to the patient's blood supply. Thus, an infusion solution entering duct 16, via line 32, which is operatively coupled to the reservoir 34 that supplies the infusion solution, as will be explained hereinafter, may enter directly into the blood flow. The opening 30 may be located as shown presently or may be located in an alternate position 36 shown by the dotted lines.

The two additional ducts 18 and 20 communicate with the spiral channel 28 at juncture points 38 and 40, respectively, thereby providing a fluid flow path into the blood stream which includes the membrane 22. Preferably the juncture points 38 and 40 occur at the opposite ends of the spiral channel.

Duct 20 is operatively coupled, via a tube 42, and a pump 44 to the reservoir 34. The pump 44 produces an underpressure (vacuum) at its input side, thus drawing the blood which passes alongside membrane 22 through the filter into the duct 20. Once filtered the filtrate will enter the reservoir 34 which has disposed therein a membrane 46. The underpressure of pump 44 is distributed over the inner surface of membrane 22 by means of the spiral channel 28 thereby providing a rather effective filtering area.

The filtrate is obtained continuously from the blood stream and includes water and low to middle molecular weight substances dissolved therein including the nurniiferous substances which are to be removed. The composition of the filtrate would depend upon the type of membrane and its filtration characteristics.

The filtrate thus obtained is permitted to flow into the right hand portion 48 of the reservoir 34. Since the reservoir 34 is separated into two halves by a flexible but fluid tight membrane 46 the volume of fluid entering the right-hand half displaces an equal amount of fluid out of the left-hand half 50. The displaced fluid flows through line or tube 32 into duct 16 out of opening 30 and into the blood stream of the patient.

Initially the left-hand half 50 of the balance reservoir 34 is completely filled with infusion solution so that the membrane 46 completely abuts the right-hand reservoir wall 52. As the filtrate enters the right-hand half the membrane is deflected completely over to the left-hand wall 54 until the fluid is completely removed from the reservoir. Once this takes place the reservoir must be replaced by a new one filled with infusion solution.

Because of the mode of operation of the balance reservoir 34 the amount of filtrate removed from the blood stream will always be replaced with the exact amount of fluid withdrawn from it. In order to remove a quantity of fluid from the patient to simulate the natural functioning of the kidneys, provision has been incorporated in the present system to upset the described equilibrium. This is accomplished by drawing off a portion of the filtrate from the right-hand half of the balance reservoir 34, via pump 54 which sucks the filtrate from the right half portion 48 of reservoir 34, via tube 56, and feeds it, via a tube 58, into container 60. The portion of filtrate removed into container 60 thus remains ineffective for balancing in the reservoir 34. In addition, a fluid may be supplied to the system from a rinsing solution container 62, via a pump 64, and tubes 66 and 68.

Tube 68 is operatively coupled to duct 18 which communicates with the spiral channel 28. The rinsing solution fluid inhibits the coagulation or a thrombolytic effect and bacteriostatic or bactericidal action and above all serves to eliminate the growth of germs causing disease or illness in the catheter during its length of use. This rinsing solution entering the spiral channel 28 flows together with the filtrate on the inner inside of the membrane 22 until it is finally conveyed into the right-hand half 48 of the balance reservoir 34, via the tube 42 and the pump 44. This additional fluid is taken into account in the total balancing of the system.

In order to insure that the vein into which the catheter is inserted is kept open, a sheath 70 may be utilized with the body portion of the catheter 12. The sheath 70, when inserted into a vein, prevents the vein from collapsing, thus insuring a continuous blood flow. The inner diameter of the sheath 70 is larger than the outer diameter of the catheter 12, thus permitting the continuous flow of fluid around the catheter 12 once it is inserted into the sheath 70.

An alternate construction of the body portion of the catheter may be found in patent application Ser. No. 928,914, entitled, "Catheter Device For Continuous Chemical Analysis Of Body Fluids" by J. G. Schindler and W. Schael, which has been filed simultaneously herewith and is incorporated herein by reference.

The catheter 12 may be introduced for example into one of the patient's large veins and may reside there for several months since the semi-permeable membrane 22 is quite durable. The external fluid system including the pumps 44, 54 and 64 and the containers 60 and 62 and reservoir 34 may be constructed in a compact form and can be affixed to a suitable area of the patient's body.

Hereinbefore has been disclosed a portable artifical kidney, for continuous use in a living being which is efficient, small in size and has an extended life expectancy. It will be understood that various changes in the details, materials, arrangement of parts and operating conditions which have been herein described and illustrated in order to explain the nature of the invention may be made by those skilled in the art within the principles and scope of the invention.

Having thus set forth the nature of the invention, what is claimed is:

1. A portable diafiltration system for use as an artificial kidney in the circulating blood stream of a living being comprising:
   (a) catheter filter means adapted to be inserted into the circulating blood stream members of said living being for obtaining a continuous flow of filtered liquid, said catheter filter means including;
      (i) a solid body portion having a least three ducts therein, each said ducts having an opening communicating with the surface of said body portion for providing a liquid flow path thereto;
      (ii) a semi-permeable membrane means circumscribing part of said body portion and covering at least two of said duct openings for filtering said blood stream and providing a filtrate;
   (b) suction means operatively coupled to the first of said membrane covered ducts for drawing off said filtrate;
   (c) reservoir means operatively coupled to said suction means and communicating with the uncovered duct, said reservoir means discharging its contents into said uncovered duct in an amount essentially equal to the amount of said filtrate received into said reservoir via said first membrane covered duct; and
   (d) means operatively coupled to and communicating with the second membrane covered duct for supplying a liquid to the surface of said filter membrane in contact with said body portion.

2. A portable artificial kidney according to claim 1 further including container means operatively coupled to and communicating with said reservoir filtrate for drawing off a portion of said filtrate and for simulating normal kidney function.

3. A portable kidney according to claim 1 wherein the discharge opening of said uncovered duct is located at one end of said catheter.

4. A portable kidney according to claim 1 wherein the discharge opening of said said second membrane covered duct is disposed on the side of said catheter proximate one end thereof.

5. A portable kidney according to claim 1 wherein said reservoir means includes a membrane disposed therein dividing said reservoir into two portions, said membrane preventing the passage of fluid thereacross, one side of said reservoir membrane communicating with said filtrate and the other side of said membrane communicating with stored reservoir contents said stored reservoir contents flowing into said uncovered duct, the amount of said filtrate entering said reservoir means being substantially equal to the amount of stored reservoir contents leaving said reservoir means.

6. A portable kidney according to claim 1 wherein said supplied liquid is a rinsing solution.

7. A portable kidney according to claim 1 further including removable sheath means adapted to be inserted into one of said blood stream members for keeping said blood stream flowing, said sheath having an inner diameter greater than the outer diameter of said catheter and being adapted to receive said catheter therein.

8. A portable kidney according to claim 1 wherein said body portion is provided with channels communicating with said covered ducts, said channels being disposed beneath said membrane and about the circumference of said body portion for providing a continuous liquid flow path.

9. A portable kidney according to claim 8 wherein said channels are in the form of a spiral.

* * * * *